United States Patent [19]

Carr

[11] Patent Number: 5,044,463
[45] Date of Patent: Sep. 3, 1991

[54] MOLDED FOAM EARPLUG AND METHOD FOR MAKING SAME

[75] Inventor: John W. Carr, Zionsville, Ind.

[73] Assignee: Cabot Corporation, Waltham, Mass.

[21] Appl. No.: 443,142

[22] Filed: Nov. 30, 1989

[51] Int. Cl.⁵ .............................................. H61B 7/02
[52] U.S. Cl. ..................... 181/135; 128/864
[58] Field of Search ....................... 181/129, 130, 135; 128/864–868

[56] References Cited

U.S. PATENT DOCUMENTS

| Re. 29,487 | 12/1977 | Gardner . | |
|---|---|---|---|
| D. 264,249 | 5/1982 | Leight | D24/67 |
| 797,509 | 8/1905 | Frank | 128/864 |
| 2,441,866 | 5/1948 | Cantor . | |
| 2,672,863 | 3/1954 | Leight | 128/867 |
| 3,811,437 | 5/1974 | Gardner . | |
| 4,094,315 | 6/1978 | Leight | 128/864 |
| 4,158,087 | 6/1979 | Wood | 521/137 |
| 4,253,452 | 3/1981 | Powers et al. | 128/864 |
| 4,774,938 | 10/1988 | Leight | 128/864 |

FOREIGN PATENT DOCUMENTS 0074535  12/1960  France ................................ 128/864

Primary Examiner—Brian W. Brown

[57] ABSTRACT

A bullet-shaped molded foam earplug is provided with a cavity extending from the flanged base axially into the earplug. The cavity provides the earplug a lower equilibrium pressure making the earplug more comfortable. The earplug is formed in a mold having a base containing a plurality of spaced apart cavities. A top plate having a plurality of pins is fitted onto the base such that the pins enter the mold and define the cavity of each earplug.

15 Claims, 2 Drawing Sheets

MOLDED FOAM EARPLUG AND METHOD FOR MAKING SAME

BACKGROUND OF THE INVENTION

1. Field of the Invention

The present invention relates to the field of earplugs and more particularly to the field of molded foam earplugs.

2. Description of the Prior Art

Foam earplugs have been developed which fit comfortably in the ear and provide desired sound attenuation. Examples of these earplugs are disclosed in U.S. Pat. No. 3,811,437 to Ross Gardner, Jr. which later reissued as U.S. Pat. No. Re. 29,487. Gardner teaches that a variety of resilient polymeric foams can be used. The foam has a sufficiently high concentration of organic plasticizer which permits the plug to be compressed and inserted into the ear canal. After insertion the plug recovers to exert an equilibrium pressure within the comfort range of the wearer. Louis Wood in his U.S. Pat. No. 4,158,087 discloses a polyurethane, latex foam which can be used for foam earplugs. Following the teaching of these patents, several companies have made and sold resilient foam earplugs.

Resilient foam earplugs have been made in a variety of shapes. Cylindrical earplugs are commonly used as are generally conical, and bullet-shaped plugs. The bullet-shaped plugs are sometimes provided with a concave flanged base which does not go into the ear canal. The only constraint to the shape of the plug is that the plug must be able to be compressed to a size smaller than the ear canal so that the plug can be inserted into the ear canal, there expand to seal the ear canal and exert a comfortable, yet effective, pressure against the wall of the ear canal.

Foam earplugs have been punched from sheets of foam and molded. In order to produce an earplug with a contoured shape, it is preferable that the plug be formed in a mold. Cantor in U.S. Pat. No. 2,441,866 discloses a bullet shaped rubber earplug having a hollow interior. The Cantor earplug cannot be radially compressed. If one exerts a radial force on the Cantor earplug, the wall of the earplug will bulge in a direction normal to the force or the wall will buckle. In either event, the circumference of the earplug will not change. A bulged Cantor earplug cannot be inserted into the ear canal unless it buckles. If a buckled Cantor earplug is inserted into the ear canal, the buckle will remain and the ear canal will not be completely sealed. Cabot Corporation has made and sold a foam earplug similar in shape to the Cantor rubber earplug. Like Cantor, this was a push-in type plug that could not be radially compressed for insertion into an ear canal.

When a foam earplug is formed in a mold, there is a tendency for the foam to adhere to the mold surface and remain in the cavity of the mold. This tendency prevents easy removal of the molded foam from the mold cavity after formation. The use of pins which are suspended from a top plate and inserted into the cavity of the mold have been tried for some kinds of molded products. However, all too frequently, the pin will tear the molded product during removal from the mold. The art has not used pins in the molding of earplugs. Nor has the art recognized that pins of certain dimensions can be used to create a beneficial cavity in a molded slow recovery foam earplug.

SUMMARY OF THE INVENTION

I provide a molded foam earplug having a beneficial central cavity. The earplugs of the present invention are bullet-shaped. My earplug mold has a plurality of cavities into which pins suspended from a top plate of the mold are inserted. The pins can have a variety of shapes and extend from about 50% to 95% of depth of the mold cavity. Foam earplugs made from my mold will, therefore, have a substantial inner cavity. A foam earplug containing the cavity exerts less pressure on the ear canal than an earplug made of the same foam but having no cavity. Consequently, the cavity containing earplug is more comfortable.

Other objects and advantages of my earplug and the mold for making same will become apparent from a description of certain present preferred embodiments therefore shown in the drawings.

DESCRIPTION OF THE PREFERRED EMBODIMENT

Figure 1:
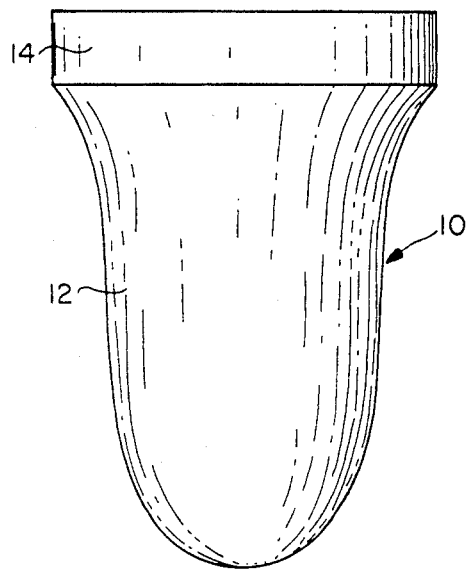
FIG. 1 is an elevational view of a present preferred embodiment of an earplug according to the invention.
Figure 2:
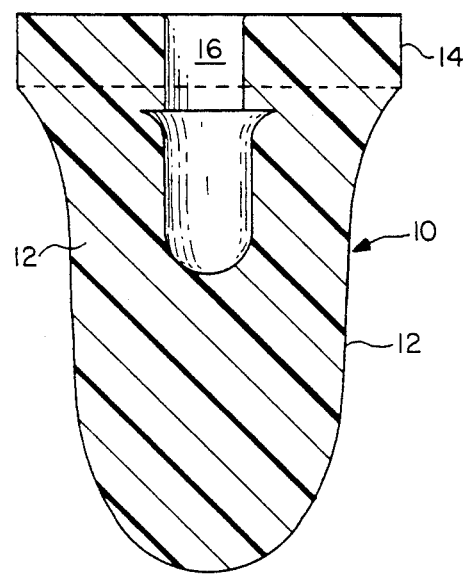
FIG. 2 is a cross-sectional view of the earplug of FIG. 1 taken along the line II—II of FIG. 1.

As shown in FIGS. 1 and 2, earplug 10 is generally bullet shaped having an end 12 adapted for insertion into the ear canal and a flanged base 14 coextensive with the end 12 and adapted to provide means for removing the earplug 10 from the ear canal. Cavity 16 extends into earplug 10 from base 14. In the embodiment of FIG. 2, cavity 16 is also bullet-shaped.

Figure 4:
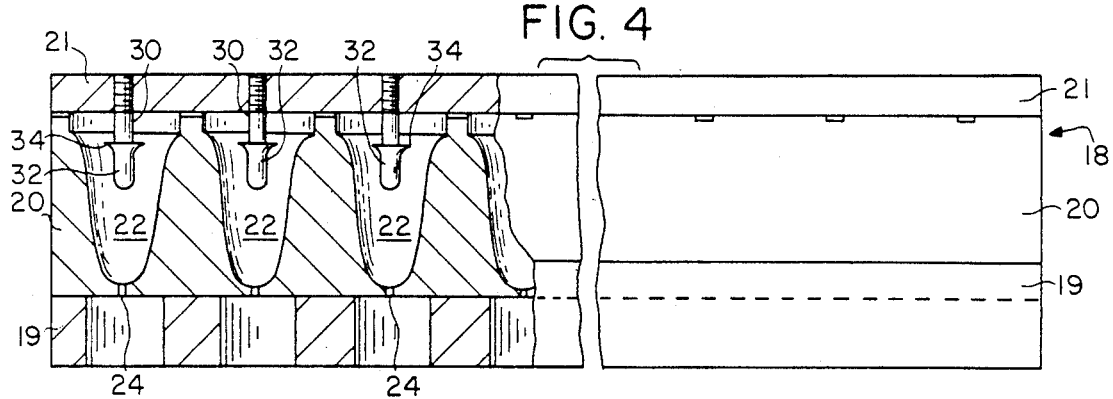
FIG. 4 is a side view partially cut away of the mold of FIG. 3.
Figure 3:
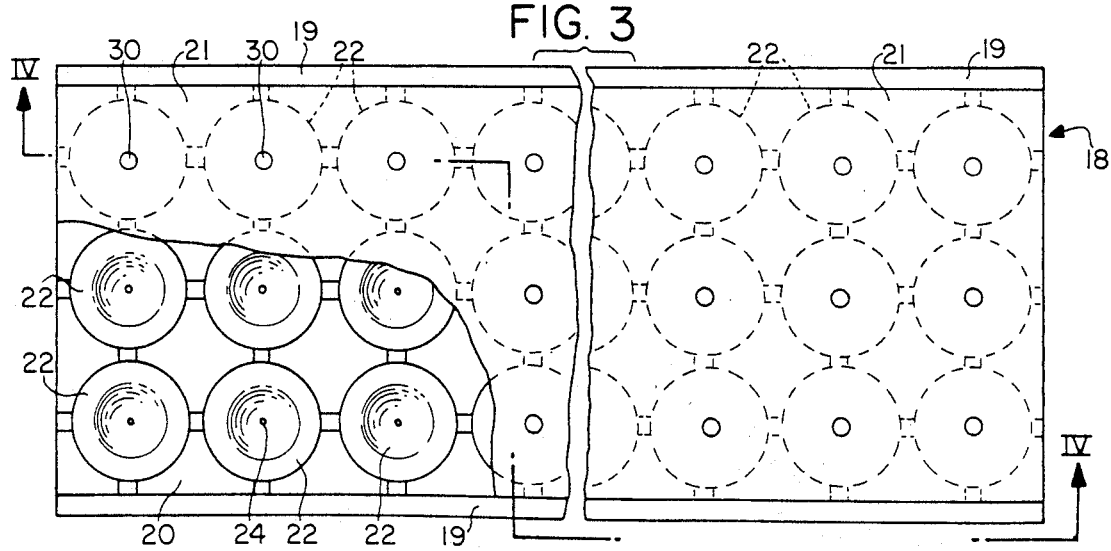
FIG. 3 is a top view partially cut away of the mold used to form the earplug of FIG. 1.

Preferably, earplug 10 is produced by injecting the constituents of a resilient foam into a three piece mold 18. As shown in FIGS. 3 and 4, mold 18 contains a plate 19, and center portion 20 and top 21 which together form a base. The center portion 20 has a plurality of cavities 22. Cavities 22 have the desired bullet-shape of earplug 10 and have a vent 24. Top plate 21 fits onto center portion 20 to form a closed mold.

A pin 30 is provided to extend from a top plate 21 and fit into each cavity 22 of mold 20. Pin end 32 is sized and configured to correspond to the desired shape of cavity 16 of earplug 10. End 32 is both thinner and shorter than cavity 22. Flange 34 can be provided on pin 30 so that when the mold is opened the formed plug will remain on pin 30. Although the pins can be used to ensure ease of removal of the earplugs from the mold, it should be noted that the important function of the pins is to produce a cavity allowing for improved comfort of any foam earplug over that which it would have had being identical but without the cavity.

After the foam ingredients have been provided in each cavity of mold 20, the top plate 21 is lowered and pins 30 are inserted into cavities 22. The ingredients react to form a foam. After the plugs 10 have been formed, the top plate 21 is lifted from the center portion 20 of the mold 18 which removes pins 30 from cavities 22. Because of the configuration of the end portion 32 and flange 34 of pin 30, plug 10 will remain attached to pin 30 after the top half 21 and attached pins 30 have been removed from cavity 22. Because foam plug 10 is deformable, the plug is easily removed from pin 30. This process is an improvement over the prior art wherein the plug 10 remained in the cavity of the the mold, thereby making removal of the plug from the mold a time consuming process.

Figure 5:
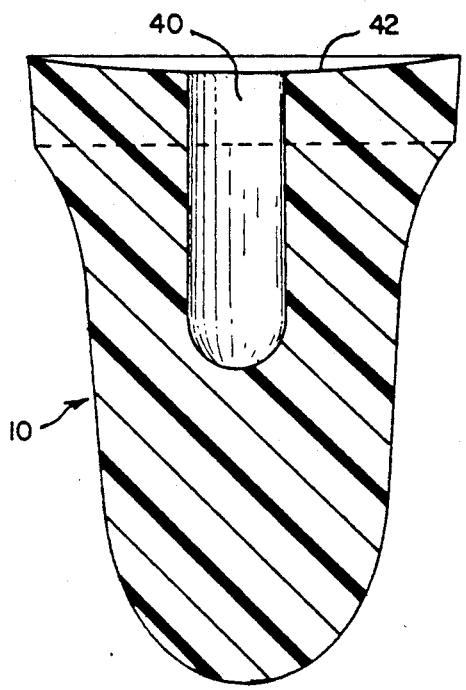
FIG. 5 is a cross-sectional view similar to FIG. 2 of an earplug having a shallow cavity.

As shown in FIGS. 5 thru 8, one can have a variety of cavity shapes and sizes each having associated advantages. The earplug 10 of FIG. 5 has a straight, shallow cavity 40. This cavity extends about 50% of the length of the earplug. The earplug of FIG. 5 can easily be stripped from the pin (not shown) used to form the cavity 40. Additionally, that pin will not interfere with foam formation during molding of the earplug. In the embodiment of FIG. 5 I also provide a concave base 42 on the earplug.

Figure 6:
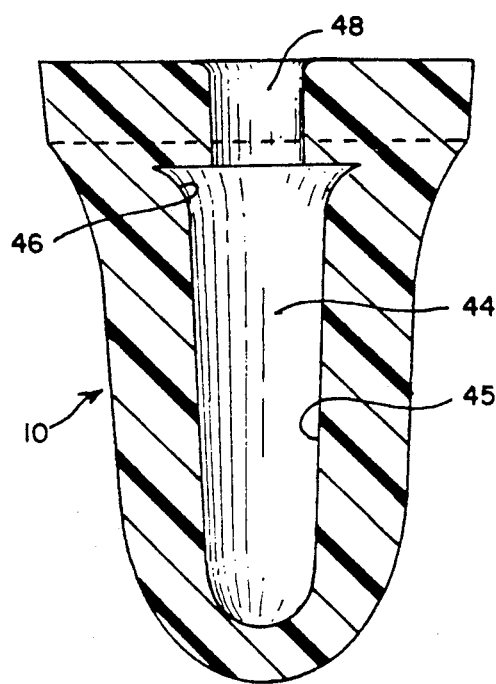
FIG. 6 is a cross-sectional view similar to FIG. 2 of an earplug having a deep cavity.

The earplug 10 of FIG. 6 has a deep cavity 44 which extends about 95% of the length of the earplug. The wall 45 of cavity 44 is tapered so that the diameter of cavity 44 decreases as you move toward the tip or nose of the earplug. A flanged portion 46 is provided near the base of cavity 44 which then necks down to a cylindrical channel 48. That smaller channel 48 is less noticable than an opening which would have been made if sloped wall 45 continued through the flanged base of the earplug. The pin used to make the cavity of the earplug of FIG. 6 would be identical to cavity 44, flanged portion 46 and channel 48. That pin has two important advantages. The sloped portion of the pin which defines wall 45 will aid polymer flow during foaming. The flanged portion will cause the earplug to adhere to the pin when the mold is opened.

Figure 7:
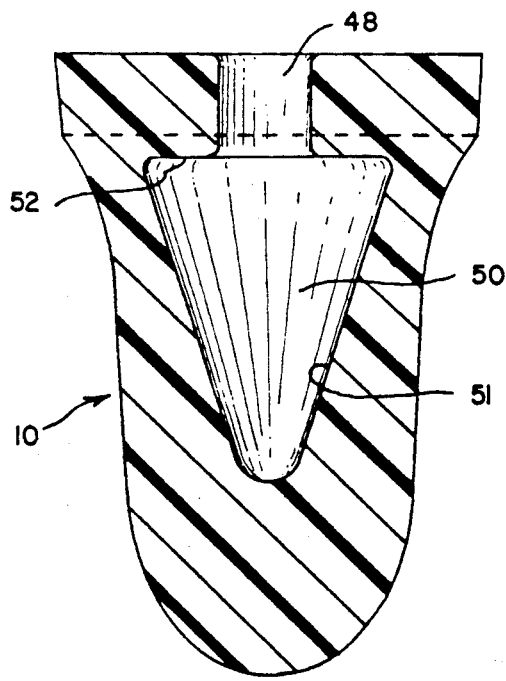
FIG. 7 is a cross-sectional view similar to FIG. 2 of an earplug having a frusto-conical cavity.

A frusto-conical cavity 50 with small channel 48 is provided in the earplug of FIG. 7. The pin used to form cavity 50 would have a sloped portion to define wall 51. That sloped portion would aid polymer flow during forming. The pin would also have a land to define wall 52. When the mold is opened the land would cause the plug to adhere to the pin.

Figure 8:
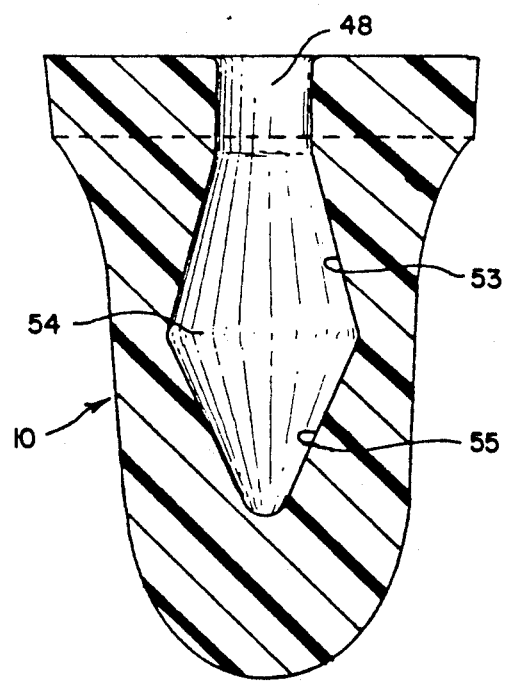
FIG. 8 is a cross-sectional view similar to FIG. 2 of an earplug having a diamond shaped cavity.

In the earplug of FIG. 8 a small channel 48 opens into a diamond shaped cavity 54. The pin used to form the diamond shaped cavity would have a first sloped portion to form wall 53 and a second sloped portion to define wall 55. During foaming the polymer should flow readily around these sloped portions. When the mold is opened the earplug of FIG. 8 should adhere to the pin that forms cavity 54. But, the sloped pin portions should permit easy removal of the plug from the pin. Indeed, removal from the pin should be easier than removal of the earplugs of FIGS. 6 and 7.

The embodiments shown in the drawings illustrate that the pin can be made so as to either ensure that the plug mechanically adheres to the pin thus enhancing earplug removal from the mold or the pin can be made so as to release from the earplug with relative ease. This may be accomplished by making the pin tapered, of substances enhancing the release such as polypropylene, polyethylene, teflon and the like or alternatively by use of mold release agents such as waxes, silicones, fluoroplastics, metallic stearates, soaps, polyethylene, fine particles of talc and many proprietary blends of chemicals.

Generally, the pin should be long enough so as to be at least 50% of the total length of the earplug, up to a length that terminates at or within the hemispherical like non-functioning tip of the bullet shaped structure without coming so close to the tip so as to allow decreased attenuation for any user. It is preferred to have the pin length between 60 to 90 percent of the total plug length. The cavity should have a diameter of sufficient size so that the earplug does not bulge when radially rolled down between the thumb and forefinger of a user. By this is meant that the earplug can be radially rolled down without the cavity flattening to a closed position such that it causes the earplug to form a large wrinkle or fold. The absence of a wrinkle or fold is essential to ensure complete ear canal sealing, i.e. maximum sound attenuation, upon insertion of the earplug into a user's ear canal. In other words, to ensure maximum comfort without detracting from desired sound attentuation, the cavity diameter should be as large as possible without causing the earplug to lap or crease when being rolled down. Generally, I found that about 0.13 inch diameter is suitable. Depending upon the material and earplug construction a diameter of about 0.19 inches will also work. For an earplug of 0.46 inches in diameter a cavity diameter from about 0.125 to 0.1875 ($\frac{1}{8}$ to 3/16) inches is acceptable.

The resulting molded earplug 10 possesses desired compressibility and recovery properties because of its unique structure. Because there is an absence of foam material in cavity 16, sidewalls 12a of earplug 10 can be readily compressed. When compressed, earplug 10 can be easily inserted into the ear canal and allowed to expand therein. Cavity 16 lowers the pressure exerted by sidewalls 18 against the ear canal making the earplug more comfortable.

In order for the earplug 10 to function properly, it should have a diameter somewhat greater than that of the average adult human ear canal. For example, an average diameter between about $\frac{3}{8}$ inch and about $\frac{3}{4}$ inch is generally acceptable. Optimally, the average diameter of earplug 10 is between 7/16 inch and 9/16 inch.

Foam earplugs with and without cavities were tested to determine the effect of the cavity upon equilibrium pressure exerted by the earplug on the ear canal. The tested foam earplugs had a length of about 0.9 inch, a flange diameter of about 0.7 inch, and an average diameter of the functional portion of about 0.46 inch. In order to aid collection of accurate data the flanges were cut off.

The cut foam earplugs were stored overnight at 50% relative humidity and 21°-24° C. After rolling the foam earplugs down by twirling between the thumb and forefinger for 20 seconds they were inserted between parallel plates spaced at a distance of 0.268 inch and the equilibrium force, in grams, was measured. Each earplug was measured four times, the results averaged and corrected for small weight differences encountered from cutting.

Experimental results in Table I show foam earplugs with shallow 0.125 inch diameter cavities yield about 17% lower exerted force. Foam earplugs with the cavity extended 0.109 inch further reaching to about the point where the spherical earplug tip begins, shows about 30% lower exerted force. Earplugs exerting lower force will be more comfortable.

I have found that the foams disclosed in Gardner Reissue Pat. No. 29,487 and Wood U.S. Pat. No. 4,158,087 can be used to form a molded earplug in accordance with this invention.

TABLE I

Equilibrium Force Measurements for Foam Earplugs With and Without Cavities

| | Orig. Wt. (gms.) | Wt. (gms.) 50% RH | Wt. (gms.) Cut | Run (Equilibrium Force) 1 | 2 | 3 | 4 | Ave. | Wt.* Corr. | SD |
|---|---|---|---|---|---|---|---|---|---|---|
| With Shallow Cavity Plug # | | | | | | | | | | |
| 1 | 0.4747 | 0.4734 | 0.2855 | 78.32 | 78.52 | 76.10 | 77.57 | 77.63 | 80.59 | |
| 2 | 0.4757 | 0.4759 | 0.3009 | 78.66 | 82.30 | 80.65 | 82.25 | 80.97 | 78.25 | |
| 3 | 0.4713 | 0.4719 | 0.2944 | 77.60 | 79.82 | 76.83 | 80.11 | 78.59 | 78.23 | |
| 4 | 0.4736 | 0.4726 | 0.2929 | 79.99 | 76.18 | 77.81 | 79.68 | 78.42 | 78.61 | 0.98 |
| | | Ave. | 0.2934 | | | | | | 78.92 | |
| Without Cavity Plug # | | | | | | | | | | |
| 1 | 0.4951 | 0.4951 | 0.3034 | 100.56 | 97.27 | 101.77 | 103.21 | 100.70 | 100.85 | |
| 2 | 0.4921 | 0.4917 | 0.2820 | 78.88 | 77.91 | 79.45 | 79.27 | 78.88 | 93.83 | |
| 3 | 0.4945 | 0.4936 | 0.2970 | 85.86 | 85.05 | 86.60 | 84.86 | 85.59 | 89.97 | |
| 4 | 0.4981 | 0.4964 | 0.3096 | 94.64 | 98.33 | 97.47 | 97.57 | 97.00 | 92.89 | |
| 5 | 0.4962 | 0.4874 | 0.3261 | 100.35 | 98.58 | 98.55 | 99.15 | 99.16 | 93.56 | |
| 6 | 0.4975 | 0.4872 | 0.3035 | 107.46 | 108.69 | 109.43 | 110.74 | 109.08 | 99.23 | |
| | | Ave. | 0.3036 | | | | | | 95.06 | 3.77 |
| With Cavity 0.109" Deeper Plug # | | | | | | | | | | |
| 1 | — | 0.4767 | 0.2851 | 69.21 | 68.56 | 69.39 | 69.68 | 69.20 | 69.66 | |
| 2 | — | 0.4752 | 0.2888 | 64.19 | 64.31 | 62.95 | 64.43 | 63.97 | 63.57 | |
| | | Ave. | 0.2870 | | | | | | 66.62 | 3.05 |

For example, a polyvinyl foam was used to form earplug 10. The mold 20 was designed such that cavity 22 has a depth of 1.104 inches and an average diameter of 0.525 inches for the tapered cylinder section of the bullet-shaped portion 12. Upper base 14 has an average diameter of 0.774 inches. In order to provide earplug 10 with the desired resilience characteristics, end 32 of pin 30 had a length of 0.1965 inches and an average diameter of 0.143 inches. Flange 34 had a diameter of 0.250 inches.

Use of the mold 18 described above produces an earplug 10 having a length of 0.894 inches and an average diameter of 0.454 inches. The diameter of flanged base 14 is 0.696 inches. Cavities of two depths were made. Both cavities had an average diameter of 0.130 inches. They had a depth of either 0.442 inches or 0.559 inches. These depths are about 50% and 63% of the plug length. Such an earplug 10 provides a comfortable fit within the ear canal of the wearer and was found to be highly effective in attenuating the transmission of 125-8000 Hertz.

While I have described certain presently preferred embodiments of my invention, it is to be distinctly understood that the invention is not limited thereto and may be otherwise variously practiced within the scope of the following claims.

I claim:

1. A molded polymeric foam earplug of generally bullet shape comprising a base at one end and a nose at an opposite end and a length therebetween, wherein said earplug has an axial cavity which extends from said base to a point located a distance from said base of between 50% to 95% of the length of said earplug, wherein said cavity has a diameter of sufficient size such that the earplug can be radially rolled down without the cavity flattening to a closed position in such a manner as to cause the earplug to form a large wrinkle or fold, wherein said rolled down earplug can be inserted into a human ear canal and there allowed to expand and obturate the ear canal.

2. The earplug of claim 1 wherein the length of said earplug is between about ½ inch and about 1 inch.

3. The earplug of claim 1 wherein the diameter of said earplug is between about ⅜ inch and about ¾ inch.

4. The earplug of claim 1 wherein the cavity is generally frusto-conical.

5. The earplug of claim 4 wherein the cavity has an average diameter of between about ⅛ inch and about 3/16 inch.

6. The earplug of claim 1 wherein the cavity has the same shape as the earplug.

7. The earplug of claim 1 wherein the cavity tapers outward and then tapers inward.

8. The earplug of claim 7 wherein the cavity is diamond shaped.

9. The earplug of claim 1 also comprising a flange coextensive with and attached to said base of said earplug.

10. The earplug of claim 9 wherein the base is concave.

11. The earplug of claim 1 wherein the base is concave.

12. The earplug of claim 1 wherein the cavity is comprised of a generally cylindrical channel and a main cavity portion having a larger diameter, said channel extending from the base to the main cavity portion.

13. The earplug of claim 1 wherein the earplug after being rolled down and placed between parallel plates spaced at a distance of 0.268 inch will yield an equilibrium force from 63 to 83 grams.

14. The earplug of claim 1 wherein said polymeric foam is a polyurethane latex foam.

15. The earplug of claim 1 wherein said polymeric foam is a homopolymer of vinyl chloride.

* * * * *